United States Patent [19]
Parekh et al.

[11] Patent Number: 6,064,754
[45] Date of Patent: May 16, 2000

[54] COMPUTER-ASSISTED METHODS AND APPARATUS FOR IDENTIFICATION AND CHARACTERIZATION OF BIOMOLECULES IN A BIOLOGICAL SAMPLE

[75] Inventors: Rajesh Bhikhu Parekh, Near Wendlebury; Robert Amess, Cumnor; James Alexander Bruce, Long Hanborough; Sally Barbara Prime, Oxford; Albert Edward Platt; Richard Michael Stoney, both of Abingdon, all of United Kingdom

[73] Assignee: Oxford Glycosciences (UK) Ltd., Abingdon, United Kingdom

[21] Appl. No.: 08/980,574

[22] Filed: Dec. 1, 1997

[30] Foreign Application Priority Data

Nov. 29, 1996 [GB] United Kingdom ............. 9624927

[51] Int. Cl.[7] ............................................. G06K 9/00
[52] U.S. Cl. ................................ 382/129; 382/153
[58] Field of Search ................................ 382/128, 129, 382/153; 364/528.01, 528.08; 702/19; 204/461, 607, 612; 436/516; 435/7.1, 288.7; 700/266, 273

[56] References Cited

U.S. PATENT DOCUMENTS

| 3,499,360 | 3/1970 | Davis ........................... 83/451 |
| 4,592,089 | 5/1986 | Hartman ....................... 382/6 |
| 5,073,963 | 12/1991 | Sammons et al. .............. 382/30 |
| 5,098,539 | 3/1992 | Shieh ........................... 204/182.8 |
| 5,217,591 | 6/1993 | Gombocz et al. ............. 204/299 R |
| 5,717,602 | 2/1998 | Kenning ....................... 364/500 |
| 5,949,899 | 9/1999 | Ng ................................. 382/129 |

FOREIGN PATENT DOCUMENTS

| 0 119 090 | 9/1984 | European Pat. Off. ....... G01N 27/26 |
| 0 119 808 | 9/1984 | European Pat. Off. ....... G01N 27/26 |

(List continued on next page.)

OTHER PUBLICATIONS

Radola, 1980, "Ultrathin–layer isoelectric focusing in 50–100 μm polyacrylamide gels on silanized glass plates or polyester films." *Electrophoresis* 1:43–56.

S.F. Zakharov, 1995, "Recovery of SDS–Protein and DNA using Commercial Automated Gel Electrophoresis Apparatus," *Applied and Theoretical Electrophoresis* 5:25–29.

Amess et al., 1995, "Programmed cell death in sympathetic neurons: A study by two–dimensional polyacrylamide gel electrophoresis using computer image analysis," *Electrophoresis* 16:1255–1267.

Appel, 1997, "Interfacing and Integrating Databases," In: *Proteome Research: New Frontiers in Functional Genomics*, pp. 149–175.

Bigge et al., 1995, "Nonselective and Efficient Fluorescent Labeling of Glycans Using 2–Amino Benzamide and Anthranilic Acid," *Analytical Biochemistry* 230:229–238.

(List continued on next page.)

*Primary Examiner*—Andrew W. Johns
*Attorney, Agent, or Firm*—Pennie & Edmonds LLP

[57] ABSTRACT

The present invention provides computer-assisted methods and apparatus for identifying, selecting and characterizing biomolecules in a biological sample. A two-dimensional array is generated by separating biomolecules present in a complex mixture. A computer-readable profile is constructed representing the identity and relative abundance of a plurality of biomolecules detected by imaging the two dimensional array. Computer-mediated comparison of profiles from multiple samples permits automated identification of subsets of biomolecules that satisfy pre-ordained criteria. Identified biomolecules can be automatically isolated from the two dimensional array by a robotic device in accordance with computer-generated instructions. A supported gel suitable for electrophoresis is provided that is bonded to a solid support such that the gel has two-dimensional spatial stability and the solid support is substantially non-interfering with respect to detection of a label, such as a fluorescent label, associated with one or more biomolecules in the gel.

26 Claims, 3 Drawing Sheets

FOREIGN PATENT DOCUMENTS

| | | | |
|---|---|---|---|
| 0 126 638 | 11/1984 | European Pat. Off. | G01N 27/26 |
| 0 162 693 | 11/1985 | European Pat. Off. | G01N 27/26 |
| 0 163 472 | 12/1985 | European Pat. Off. | G01N 27/26 |
| 0 324 539 | 7/1989 | European Pat. Off. | G01N 27/26 |
| 0 510 824 | 10/1992 | European Pat. Off. | B01D 57/02 |
| 0 555 145 | 8/1993 | European Pat. Off. | B01D 57/02 |
| 0 806 659 | 11/1997 | European Pat. Off. | G01N 27/447 |
| 30 32 069 | 3/1982 | Germany | C09D 5/40 |
| WO 93/05698 | 4/1993 | WIPO | A61B 1/00 |
| WO 93/15394 | 8/1993 | WIPO | G01N 27/447 |
| WO 95/14118 | 5/1995 | WIPO | C25B 9/00 |
| WO 95/22058 | 8/1995 | WIPO | G01N 33/552 |
| WO 96/18099 | 6/1996 | WIPO | G01N 27/447 |
| WO 96/18892 | 6/1996 | WIPO | G01N 27/447 |
| WO 96/39625 | 12/1996 | WIPO | G01N 27/447 |
| WO 97/26539 | 7/1997 | WIPO | G01N 35/00 |

OTHER PUBLICATIONS

Clauser et al., 1995, "Rapid mass spectrometric peptide sequencing and mass matching for characterization of human melanoma proteins isolated by two–dimensional PAGE," *Proc. Natl. Acad. Sci. USA* 92:5072–5076.

Ducret et al., 1996, "Characterization of human serum amyloid A protein isoforms separated by two–dimensional electrophoresis by liquid chromatography/electrospray ionization tandem mass spectrometry," *Electrophoresis* 17:866–876.

Eng et al., 1994, "An Approach to Correlate Tandem Mass Spectral Data of Peptides with Amino Acid Sequences in a Protein Database," *J. Am. Soc. Mass Spectrom.* 5:976–989.

Figeys et al., 1996, "Protein Identification by Capillary Zone Electrophoresis/Microelectrospray Ionization–Tandem Mass Spectrometry at the Subfemtomole Level," *Analytical Chemistry* 68(11):1822–1828.

Firestone and Winguth, 1990, "Immunoprecipitation of Proteins," *Methods in Enzymology* 182:688–699.

Gevaert et al., 1996, "Structural analysis and identification of gel–purified proteins, available in the femtomole range, using a novel computer program for peptide sequence assignment, by matrix–assisted laser desorption ionization—reflectron time–of–flight—mass spectrometry," *Electrophoresis* 17:918–924.

Gooley and Packer, 1997, "The Importance of Protein Co– and Post–Translational Modifications in Proteome Projects" In: *Proteome Research: New Frontiers in Functional Genomics*, pp. 65–91.

Herbert et al., 1997, "Two–Dimensional Electrophoresis: The State of the Art and Future Directions" *Proteome Research: New Frontiers in Functional Genomics*, pp. 13–33.

Hochstrasser, 1997, "Clinical and Biomedical Applications of Proteomics" In: *Proteome Research: New Frontiers in Functional Genomics*, pp. 187–219.

Hochstrasser et al., 1997, "Conclusions" In: *Proteome Research: New Frontiers in Functional Genomics*, pp. 233–237.

Jensen et al., 1997, "Protein analysis by mass spectrometry," In: *Protein Structure. A Practical Approach*, pp. 29–57.

Linn, 1990, "Strategies and Considerations for Protein Purifications," *Methods in Enzymology* 182:9–15.

Patterson and Aebersold, 1996, "Mass spectrometic approaches for the identification of gel–separated proteins," *Electrophoresis* 16:1791–1814.

Pharmacia Biotech, 1994, "Immobiline® DryStrip Kit for 2–D Electrophoresis with Immobiline® DryStrip and Excel-Gel™ SDS", Instructions (Ref. 18–1038–63, Edition AB) pp. 1–36.

Phoretix, 1997, Setting the Standard in 1D and 2D Electrophoresis, pp. 1–15.

Sanchez et al., 1997, "Improved and simplified in–gel sample application using reswelling of dry immobilized pH gradients," *Electrophoresis* 18:324–327.

Shevchenko et al., 1996, "Mass Spectrometric Sequencing of Proteins from Silver–Stained Polyacrylamide Gels," *Analytical Chemistry* 68(5):850–858.

Starr et al., 1996, "Fluorophore–assisted carbohydrate electrophoresis in the separation, analysis, and sequencing of carbohydrates," *Journal of Chromatography A* 720:295–321.

Takahashi, 1996, "Three Dimensional Mapping of N–Linked Oligosaccharides Using Anion–Exchange, Hydrophobic and Hydrophilic Interaction Modes of High–Performance Liquid Chromatography," *Journal of Chromatography A* 720:217–225.

Westermeier, 1997, "Method 10: IEF in immobilized pH gradients" In: *Electrophoresis in Practice: A Guide to Theory and Practice*, pp. 197–214.

Wilkins and Gooley, 1997, "Protein Identification in Proteome Projects" In: *Proteome Research: New Frontiers in Functional Genomics*, pp. 35–64.

Williams and Hochstrasser, 1997, "Introduction to the Proteome" In: *Proteome Research: New Frontiers in Functional Genomics*, pp. 1–12.

Williams and Pallini, 1997, "Biological Applications of Proteomics" In: *Proteome Research: New Frontiers in Functional Genomics*, pp. 221–232.

COMPUTER-ASSISTED METHODS AND APPARATUS FOR IDENTIFICATION AND CHARACTERIZATION OF BIOMOLECULES IN A BIOLOGICAL SAMPLE

1. INTRODUCTION

This invention relates to computer-assisted methods and apparatus for efficiently and systematically studying molecules that are present in biological samples and determining their role in health and disease. In particular, this invention relates to the emerging field of proteomics, which involves the systematic identification and characterization of proteins that are present in biological samples, including proteins that are glycosylated or that exhibit other post-translational modifications. The proteomics approach offers great advantages for identifying proteins that are useful for diagnosis, prognosis, or monitoring response to therapy and in identifying protein targets for the prevention and treatment of disease.

2. BACKGROUND OF THE INVENTION

Recent advances in molecular genetics have revealed the benefits of high-throughput sequencing techniques and systematic strategies for studying nucleic acids expressed in a given cell or tissue. These advances have highlighted the need for operator-independent computer-mediated methods for identifying and selecting subsets or individual molecules from complex mixtures of proteins, oligosaccharides and other biomolecules and isolating such selected biomolecules for further analysis.

Strategies for target-driven drug discovery and rational drug design require identifying key cellular components, such as proteins, that are causally related to disease processes and the use of such components as targets for therapeutic intervention. However, present methods of analyzing biomolecules such as proteins are time consuming and expensive, and suffer from inefficiencies in detection, imaging, purification and analysis.

Though the genomics approach has advanced our understanding of the genetic basis of biological processes, it has significant limitations. First, the functions of products encoded by identified genes—and especially by partial cDNA sequences—are frequently unknown. Second, information about post-translational modifications of a protein can rarely be deduced from a knowledge of its gene sequence, and it is now apparent that a large proportion of proteins undergo post-translational modifications (such as glycosylation and phosphorylation) that can profoundly influence their biochemical properties. Third, protein expression is often subject to post-translational control, so that the cellular level of an mRNA does not necessarily correlate with the expression level of its gene product. Fourth, automated strategies for random sequencing of nucleic acids involve the analysis of large numbers of nucleic acid molecules prior to determining which, if any, show indicia of clinical or scientific significance.

For these reasons, there is a need to supplement genomic data by studying the patterns of protein and carbohydrate expression, and of post-translational modification generally, in a biological or disease process through direct analysis of proteins, oligosaccharides and other biomolecules. However, technical constraints have heretofore impeded the rapid, cost-effective, reproducible, systematic analysis of proteins and other biomolecules present in biological samples.

3. SUMMARY OF THE INVENTION

The present invention is directed to efficient, computer-assisted methods and apparatus for identifying, selecting and characterizing biomolecules in a biological sample. According to the invention, a two-dimensional array is generated by separating biomolecules present in a complex mixture. The invention provides a computer-generated digital profile representing the identity and relative abundance of a plurality of biomolecules detected in the two-dimensional array, thereby permitting computer-mediated comparison of profiles from multiple biological samples. This automatable technology for screening biological samples and comparing their profiles permits rapid and efficient identification of individual biomolecules whose presence, absence or altered expression is associated with a disease or condition of interest. Such biomolecules are useful as therapeutic agents, as targets for therapeutic intervention, and as markers for diagnosis, prognosis, and evaluating response to treatment. This technology also permits rapid and efficient identification of sets of biomolecules whose pattern of expression is associated with a disease or condition of interest; such sets of biomolecules provide constellations of markers for diagnosis, prognosis, and evaluating response to treatment.

The high throughput, automatable methods and apparatus of the present invention further permit operator-independent selection of individual separated biomolecules (or subsets of separated biomolecules) according to pre-ordained criteria, without any requirement for knowledge of sequence information or other structural characteristics of the biomolecules. This in turn provides automated, operator-independent isolation and parallel characterization of a plurality of selected biomolecules detected in a biological sample. Thus, the present invention advantageously permits automated selection of biomolecules prior to sequencing or structural characterization. In one particular embodiment, the present invention provides a gel that is suitable for electrophoresis of biomolecules (such as proteins) and is bonded to a solid support such that the gel has two-dimensional spatial stability and the support is substantially non-interfering with respect to detection of a label associated with one or more biomolecules in the gel (e.g. a fluorescent label bound to one or more proteins). In another particular embodiment, the invention provides an integrated computer program that compares digital profiles to select one or more biomolecules detected in a two-dimensional array and generates instructions that direct a robotic device to isolate such selected biomolecules from the two dimensional array. In yet a further embodiment, the program also implements a laboratory information management system (LIMS) that tracks laboratory samples and associated data such as clinical data, operations performed on the samples, and data generated by analysis of the samples.

4. BRIEF DESCRIPTION OF THE FIGURES

5. DETAILED DESCRIPTION OF THE INVENTION

Figure 1:
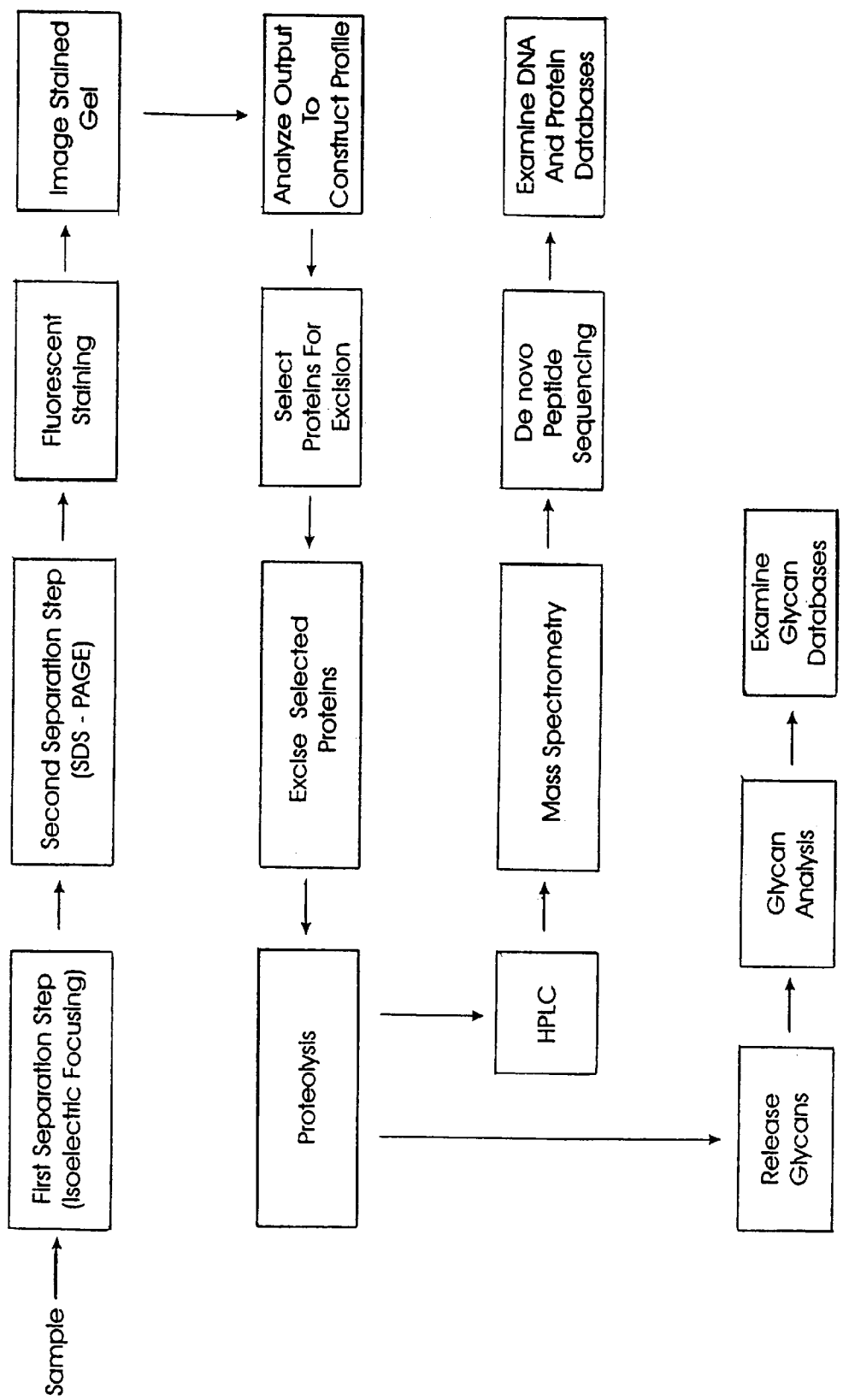
FIG. 1 is a flow diagram of operations that are performed on a mixture of different proteins according to a particular embodiment of the present invention.

The present invention provides methods and apparatus for rapidly and efficiently identifying and characterizing biomolecules, for example proteins, in a biological sample.

In one application of the invention, a biological sample is subjected to two successive separation steps. In the first separation step, the biomolecules are separated according to one physical or chemical property so as to generate a one-dimensional array containing the biomolecules; for example, proteins are separated by isoelectric focusing along a first axis. In the second separation step, the biomolecules in this one-dimensional array are separated according to a second physical or chemical characteristic so as to generate a two-dimensional array of separated biomolecules; for example, proteins separated by isoelectric focusing are subjected to SDS-PAGE along a second axis perpendicular to the first axis. The separated biomolecules are stably maintained in the two-dimensional array for subsequent imaging. The stable two-dimensional array can be stored or archived for an extended period (e.g. months or years) and selected biomolecules can be retrieved from the array at any desired time, based on automated computer analysis of the data derived from imaging.

The two-dimensional array is imaged with a detector to generate a computer-readable output that contains a set of x,y coordinates and a signal value for each detected biomolecule. If desired, the computer-readable output can be displayed to a human operator—before or after computer-mediated analysis—as a computer-generated image on a screen or on any suitable medium. Computer-mediated analysis of the computer-readable output is performed, resulting in a computer-readable profile that represents, for a plurality of detected biomolecules, the relative abundance of each such biomolecule and its attributes as deduced from its x,y coordinates in the two-dimensional array. For example, a profile derived from imaging a gel containing proteins separated by isoelectric focusing followed by SDS-PAGE represents the isoelectric point (pI), apparent molecular weight (MW) and relative abundance of a plurality of detected proteins.

The computer-readable profiles of the present invention are suitable for computer-mediated analysis to identify one or more biomolecules that satisfy specified criteria. In one embodiment, a first set of profiles is compared with a second set of profiles to identify biomolecules that are represented in all the profiles of the first set (or in a first percentage of the profiles of the first set) and are absent from the profiles of the second set (or are absent from a second percentage of the profiles of the second set, where the first and second percentages can be independently specified). In other embodiments, sets of profiles are compared to identify biomolecules that are present at a designated higher level of expression in a specified percentage of profiles of one sample set than in a specified percentage of profiles of another sample set, or to identify biomolecules whose post-translational processing differs from one sample set to another.

One or more biomolecules so identified are selected for isolation. In one embodiment, this selection is made automatically by a computer, in accordance with pre-ordained programmed criteria, without further human intervention. In another embodiment, a human operator reviews the results of the computer-mediated analysis and then enters a selection into a computer. For isolation of each selected biomolecule, a computer generates machine-readable instructions that direct a robotic device (a) to remove one or more portions of the two-dimensional array that contain the selected biomolecule and (b) to deliver the removed portions to one or more suitable vessels for further characterization. For example, a selected protein can be analyzed to determine its full or partial amino acid sequence, to detect and characterize any associated oligosaccharide moieties, and to study other aspects of post-translational processing, e.g. phosphorylation, myristylation and the like. The invention advantageously permits automated parallel processing of biomolecules removed from the two-dimensional array, thereby facilitating rapid and efficient characterization of a plurality of selected biomolecules. FIG. 1 presents a flowchart illustrating processing of a sample according to one particular embodiment of the present invention.

The present invention is useful for identifying and analyzing proteins, but is more generally applicable to the identification and analysis of any biomolecule. As used herein, the term "biomolecule" refers to any organic molecule that is present in a biological sample, and includes peptides, polypeptides, proteins, oligosaccharides, lipids, steroids, prostaglandins, prostacyclines, and nucleic acids (including DNA and RNA). As used herein, the term "protein" includes glycosylated and unglycosylated proteins.

5.1. Biological Samples

As used herein, the term "biological sample" refers to any solid or fluid sample obtained from, excreted by or secreted by any living organism, including single-celled microorganisms (such as bacteria and yeasts) and multicellular organisms (such as plants and animals, for instance a vertebrate or a mammal, and in particular a healthy or apparently healthy human subject or a human patient affected by a condition or disease to be diagnosed or investigated). A biological sample may be a biological fluid obtained from any site (e.g. blood, plasma, serum, urine, bile, cerebrospinal fluid, aqueous or vitreous humor, or any bodily secretion), a transudate, an exudate (e.g. fluid obtained from an abscess or any other site of infection or inflammation), or fluid obtained from a joint (e.g. a normal joint or a joint affected by disease such as rheumatoid arthritis, osteoarthritis, gout or septic arthritis). Alternatively, a biological sample can be obtained from any organ or tissue (including a biopsy or autopsy specimen) or may comprise cells (whether primary cells or cultured cells) or medium conditione-d by any cell, tissue or organ. If desired, the biological sample may be subjected to preliminary processing, including preliminary separation techniques. For example, cells or tissues can be extracted and subjected to subcellular fractionation for separate analysis of biomolecules in distinct subcellular fractions, e.g. proteins or drugs found in different parts of the cell. See Deutscher (ed.), 1990, Methods In Enzymology vol. 182, pp. 147–238 (incorporated herein by reference in its entirety). Similarly, immunoprecipitation can be performed to identify antigenically related biomolecules such as proteins. See Firestone & Winguth In Duetscher, op. cit. pp. 688–699 (incorporated herein by reference in its entirety).

Preferably, relevant clinical information useful to the analysis is catalogued and indexed to the corresponding sample; a computer-based laboratory information management system (LIMS) is preferred for this purpose. Such information preferably includes patient data such as family history, clinical diagnosis, gender, age, nationality, place of residence, place of employment, and medical history. Information related to the sample itself is also preferably indexed in the LIMS; such information can include the sample type, the precise location from which the sample was taken, the day and time that the sample was taken, the time between collection and storage, the method of storage, and the procedure used to obtain the sample.

Methods of indexing the information record to the proper sample can include the assignment of matching numbers to the record and the sample. This process is preferably automated through the use of barcodes and a barcode scanner. As each sample is processed, the scanner is used to record the sample identification number into the LIMS, which tracks the sample through its various manipulations, thus preserving the link between record and sample. The use of barcodes also permits automated archiving and retrieval of stored samples and gels.

5.2. Analysis of Proteins

In one embodiment, the methods and apparatus of the present invention are used to identify and characterize one or more proteins in a biological sample or samples.

5.2.1. First Separation Step

A wide variety of techniques for separating proteins are well known to those skilled in the art, see, e.g., Deutscher (ed.), 1990, Methods In Enzymology vol. 182, pp. 9–18 and 285–554 (incorporated herein by reference in its entirety) and may be employed according to the present invention. By way of example, and not of limitation, proteins may be separated on the basis of isoelectric point (e.g. by chromatofocusing or isoelectric focusing), of electrophoretic mobility (e.g. by non-denaturing electrophoresis or by electrophoresis in the presence of a denaturing agent such as urea or sodium dodecyl sulfate (SDS), with or without prior exposure to a reducing agent such as 2-mercaptoethanol or dithiothreitol), by chromatography, including FPLC and HPLC, on any suitable matrix (e.g. gel filtration chromatography, ion exchange chromatography, reverse phase chromatography or affinity chromatography, for instance with an immobilized antibody or lectin), or by centrifugation (e.g. isopycnic centrifugation or velocity centrifugation).

Any separation technique, including any technique enumerated above, can be used in the first separation step. In one embodiment, the first separation step results in a discontinuous one-dimensional array (e.g. fractions collected during affinity chromatography). More preferably, the first separation step results in a continuous one-dimensional array; especially preferred is isoelectric focusing in a polyacrylamide strip gel provided with appropriate electrolytes.

5.2.2. Second Separation Step

The second separation step employs a separation technique, distinct from that used in the first separation step, to generate a two-dimensional array of separated proteins. Any separation technique (including those enumerated above) can be used, and in any medium, provided that (a) the resulting two-dimensional array of biomolecules (e.g., proteins) can be imaged to detect the physical positions of a plurality of separated biomolecules in the separation medium and (b) one or more selected biomolecules can be isolated from the medium in which the second separation step was performed. In a preferred embodiment, the second separation step employs electrophoresis in a gel such as a polyacrylamide slab gel; especially preferred is polyacrylamide gel electrophoresis in the presence of sodium dodecyl sulfate (SDS-PAGE). If the first separation step results in a discontinuous one-dimensional array, fractions of the one-dimensional array (or aliquots thereof) are subjected to the second separation technique. For example, aliquots of fractions from affinity chromatography are loaded into wells of a polyacrylamide gel for SDS-PAGE. If the first separation step results in a continuous one-dimensional array, the array (or a portion thereof) is subjected to the second separation technique. For example, a strip gel containing proteins separated along a first axis by isoelectric focusing is loaded onto a polyacrylamide slab gel for SDS-PAGE along a second axis perpendicular to the first axis.

5.2.3. Supported Polyacrylamide Gels

One aspect of the present invention is a supported gel, suitable for use in electrophoresis, in which the gel is stably bonded to a solid support such that the gel has two-dimensional spatial stability, and the support is rigid and is substantially non-interfering with respect to detection of a label bound to or otherwise associated with one or more biomolecules in the gel. Preferably, the support is substantially non-interfering with respect to detection of a fluorescent label; a glass support is suitable for this purpose since glass, unlike plastic, is devoid of spectral activity that impairs or prevents fluorescence imaging.

By virtue of the stable bond between the gel and the solid support, one or more portions of the gel can now be removed (e.g. by excision) without positional shift of the remainder of the gel, or with only minimal distortion, thereby maintaining the integrity of the two-dimensional array of separated proteins during manipulation and storage; preferably, the gel is covalently bonded to the solid support. Following imaging to determine the x,y coordinates of the separated proteins, one or more portions of the supported gel containing selected proteins can be removed for further analysis while the remaining proteins are stably held in their previously imaged locations for subsequent removal if desired. The supported gel of the present invention represents a major advance in facilitating the accurate, reproducible excision and isolation of separated biomolecules. Moreover, the supported gel can be barcoded to provide an inseparable link between the identity of the original sample and the two-dimensional array of separated biomolecules; such a link can be maintained using the LIMS of the present invention.

To prepare the supported gel, a solid support can be functionalized, for instance with a bifunctional linker such as γ-methacryl-oxypropyltrimethoxysilane; the gel is then cast on the functionalized support. In a preferred embodiment, the support is generally planar, (e.g. a generally planar sheet of glass); especially preferred is a flat sheet of glass. If desired, the supported gel can be stored, for instance at reduced temperature (e.g. at 4° C., –20° C., or –70° C.). A suitable method of storage is described in International Patent Application No. PCT/GB97/01846, filed Jul. 9, 1997, which is incorporated herein by reference in its entirety. For some operations (e.g. excision of one or portions of the gel) an open-faced supported gel is preferred; for other operations (e.g. electrophoresis) the gel can optionally be sandwiched between a first solid support to which the gel is stably bonded (e.g. a glass plate treated with a bifunctional linker) and a second solid support to which the gel is not stably bonded (e.g. an untreated glass plate or a glass plate treated with a siliconizing agent).

5.2.4. Detection of Separated Proteins

The proteins in the two-dimensional array can be detected by any desired technique. In one embodiment, proteins in a polyacrylamide gel are labelled with a suitable dye (such as Coomassie Blue or a fluorescent dye) or by a suitable staining technique (such as silver staining), as is well known in the art. In a preferred embodiment, proteins in a polyacrylamide gel are labelled by impregnating the gel with a dye that becomes fluorescently active or alters its fluorescence properties when it binds to or contacts a protein, thereby obviating the need to remove unbound dye prior to imaging; Sypro Red (Molecular Bioprobes, Inc., Eugene, Oreg.) is suitable for this purpose. In another embodiment, the proteins can be labelled by impregnating the gel with an antibody, lectin or other suitable ligand that is associated with a reporter moiety such as a radionuclide, an enzyme, or a binding species such as biotin; upon removal of unbound antibody, lectin or other ligand, the reporter species can be detected by any suitable technique. In a further embodiment, proteins are radiolabelled prior to separation, for instance by metabolic labeling with any suitable radionuclide (e.g. tritium, a radionuclide of sulfur or a radionuclide of carbon) or by chemical or enzymatic labeling with any suitable radionuclide (e.g. radio-iodine). In yet a further embodiment, the proteins are electro-transferred to a suitable membrane to form a replica of the two-dimensional array that is probed with an antibody, lectin, or other suitable ligand associated with a reporter moiety; techniques for such Western blotting are well known in the art.

The labelled proteins are imaged with any detector that is capable of detecting the reporter species used—for instance by densitometry or spectroscopy, or by detecting fluorescence or radioactivity—and that generates a computer-readable output. In one embodiment, the detector is a laser fluorescence scanner in which a rotating mirror scans a laser beam across a gel along a first axis while the gel is advanced along a second axis orthogonal to the first axis. Such a scanner, in which a gel is transported linearly over a continuously scanning laser, enables gels to be loaded automatically from a hopper (e.g. a staining tank) onto the transport mechanism, scanned, and automatically encapsulated after the scan has been completed, thereby improving throughput and reducing manual handling of the gels. Preferably, the fluorescence emitted by the gel enters a wave guide and is conveyed to a photodetector such as a photomultiplier tube. In one embodiment, the laser beam travels from the rotating mirror along a plane parallel to the gel until it reaches a second mirror of arcuate shape that reflects it to strike the gel at a right angle. By virtue of the arcuate mirror, the path length of the laser beam remains constant while the gel is scanned from one side to the other. This constant path length facilitates phase-sensitive detection, in which the amplitude of the laser beam is cyclicly modulated; the fluorescence signal emitted by a protein-dye complex (signal) shows a phase shift that is used to distinguish this signal from background fluorescence (noise), in which no phase shift (or a lesser phase shift) is observed. Such a laser fluorescence scanner is described in Basiji, 1997, Development of a High-Throughput Fluorescence Scanner Employing Internal Reflection Optics And Phase-Sensitive Detection (Ph.D. Thesis, University of Washington, Seattle, Wash.), which is incorporated herein by reference in its entirety.

It is desirable to provide one or more reference points, detectable by the imaging device, for use in determining the x,y, coordinates of any features detected in the two-dimensional array of separated proteins. Reference points can be provided on a support (e.g. a functionalized generally planar glass surface) to which a gel is covalently attached. Alternatively, reference points can be provided on a frame to which a gel is fixed during imaging; a matching frame can be provided in a robotic isolation device.

5.3. Analysis of Oligosaccharides

Oligosaccharides (glycans) in a biological sample can be identified and characterized with the methods and apparatus of the present invention, using established techniques for cleaving, labelling and separating oligosaccharides. See, e.g., Townsend & Hotchkiss (eds.), 1997, Techniques in Glycobiology (Marcel Dekker, Inc., New York); Takahashi, 1996, J. Chromatography 720: 217–225, each of which is incorporated herein by reference in its entirety.

In a preferred embodiment, oligosaccharides are fluorescently labelled (e.g. with ortho-substituted aniline derivatives such 2-amino benzamidine or 2-anthranilic acid) and are separated by two-dimensional polyacrylamide gel electrophoresis. See Starr et al., 1996, J. Chromatography 720: 295–321; Bigge et al., 1995, Analyt. Biochem. 230: 229–238 (each of which is incorporated herein by reference in its entirety). For example, fluorescently labelled oligosaccharides can be subjected to polyacrylamide gel electrophoresis (PAGE) in a first dimension (e.g. using a 15% acrylamide gel and a Tris (hydroxymethyl) amino methane ("Tris")/N-tris (hydroxymethyl) methyl-3-amino propane sulfonic acid ("TAPS") buffer, pH 7.4) in order to achieve separation based largely on the intrinsic charge-to-mass ratio of the oligosaccharides. This one-dimensional array of oligosaccharides is then subjected to PAGE in a second dimension, using a 20% acrylamide gel and a 20 mM Tris/borate buffer, pH 8.5, in order to achieve separation based largely on induced charge arising from non-covalent complexation of the borate anion with the oligosaccharides. The oligosaccharides in the resulting two-dimensional array are imaged with a fluorescent scanner to generate a computer-readable output.

5.4. Computer Analysis of the Detector Output

The present invention advantageously provides for computer-mediated analysis of the detector output. By way of example, but not of limitation, this aspect of the invention is discussed in the context of proteins separated first by isoelectric focusing and then by SDS-PAGE; however, it will be readily apparent to one of skill in the art that the method and apparatus herein described are equally applicable to analysis of the output derived from imaging any two-dimensional array of separated biomolecules.

To transfer the output for analysis, the detector is operably connected to a computer. As used herein, the term "operably connected" includes either a direct link (e.g. a permanent or intermittent connection via a conducting cable, an infra-red communicating device, or the like) or an indirect link whereby the data are transferred via an intermediate storage device (e.g. a server or a floppy disk). It will readily be appreciated that the output of the detector should be in a format that can be accepted by the computer. A bitmap format (e.g. GIF format) is preferred for this purpose.

Once transferred to an appropriately programmed computer, the output can be processed to detect reference points; to filter and remove artifacts; to detect and quantify features; and to create image files. Features can be detected by a computer-mediated comparison of potential protein spots with the background. For example, the computer program can select signals corresponding to areas of the gel which display staining or fluorescence that exceeds a given threshold.

Moreover, a computer can be used to edit the features detected and to match duplicate analyses of a given sample (or any number of replicates). Outputs can be evaluated and compared to reject image files which have gross abnormalities, or are of too low a loading or overall image intensity, or are of too poor a resolution, or where duplicates are too dissimilar. If one image file of a duplicate is rejected then the other image file belonging to the duplicate is also rejected regardless of image quality. Any of these functions can be performed automatically according to operator-determined criteria, or interactively, upon displaying an image file to a human operator.

Landmark identification can be used to correct for any variability in the running of the gel. This process involves the identification of one or more landmark proteins that are known or expected to be found in a given biological sample with a constant isoelectric point and electrophoretic mobility. These landmark proteins can serve as endogenous standards to correct for any possible gel variation or distortion.

Alternatively, or in addition, one or more proteins can be added to the sample to serve as exogenous standards. Features that are considered to be artifacts can be filtered out of the analysis; such artifacts are likely to occur mainly at the edges of the gel and particularly at or near the sample application point and the dye-front.

If desired, output from two or more experiments can be aligned and combined to form a panoramic image file; for example, a sample comprising proteins can be separated by two-dimensional electrophoresis, using an isoelectric focusing gradient from pH 4.0 to 5.0 in one experiment and an isoelectric focusing gradient from 5.0 to 6.0 in a second experiment. A computer can now be used to represent the outputs obtained from these experiments as a single panoramic image for viewing or further analysis.

Duplicate gels can be aligned via the landmarks and a matching process can be performed. The matching process can involve pairing corresponding features on the duplicate gels. This provides increased assurance that subsequently measured isoelectric points and apparent molecular weights are accurate, as paired features demonstrate the reproducibility of the separation. The processed image file can be displayed on a screen for visual inspection, printed out as a graphical representation, and used for subsequent analysis.

In one embodiment, a computer is used to measure the x,y coordinates of all detected proteins (or of a subset selected interactively or automatically according to operator-established criteria). Such coordinates are correlated with particular isoelectric points and apparent molecular weights by reference to the experimental parameters used in the separation steps, to landmark proteins, or to exogenous standards. The intensity of the signal representing the protein features is also measured and stored.

Suitable programs for image processing are well known in the art. The commercial program distributed by BioRad Laboratories, Hercules, Calif. under the trade-name MELANIE® (Release 2.2, 1997) is suitable for this purpose. In a preferred embodiment, MELANIE® is used to perform the following operations on the detector output: (a) calibration of a gel so as to transform column and row co-ordinates into isoelectric point (pI) and molecular weight (MW) values by reference to landmark definitions; (b) detection of features in the gel image; (c) pairing of features between duplicate gels; (d) calculating, for each detected feature, its absolute feature intensity (Vol.), relative feature intensity (% Vol.), pI and MW; and (e) pairing of features between gels run from different samples. The output from MELANIE can thus include feature reports, landmark reports, and pair reports.

5.5. Computer Generation and Analysis of Profiles

The output of the image processing program (e.g. MELANIE®) can be further processed with a computer to generate digital profiles suitable for comparative analysis.

5.5.1. Construction of Profiles

A digital profile can now be constructed for each image file processed by MELANIE®. In a preferred embodiment, each sample is analyzed in two or more replicates (referred to as "siblings"), of which one is arbitrarily designated as the "representative" gel for the sibling set. A digital profile preferably comprises, for each identified feature: 1) a unique arbitrary identification code, 2) the x,y coordinates, 3) the isoelectric point, 4) the molecular weight, and 5) the fluorescence intensity.

For each set of sibling gels, the feature reports from sibling images are coalesced into a synthetic composite by averaging the % Vol, the pI, and the MW between matched features. The synthetic composite then consists of the averaged feature parameters assigned to feature IDs taken from the representative gel of the sibling set. In addition, the standard deviation of the mean of % Vol is calculated by the following formula (for duplicate gels):

$$D=100*SQRT(sqr(<V>-V_1)+sqr(<V>-V_2))/<V>$$

where $<V>=(V_1+V_2)/2$, and $V_1$, $V_2$ are the % Vol values for a pair of features.

Additional information may also be associated with the synthetic composite, e.g. the total amount of protein applied to the gel, and the barcode of the gel. In a preferred embodiment, the synthetic composite comprises a feature report in MELANIE® format, referenced to the representative gel and keyed to the bar-code of the representative gel.

Figure 2:
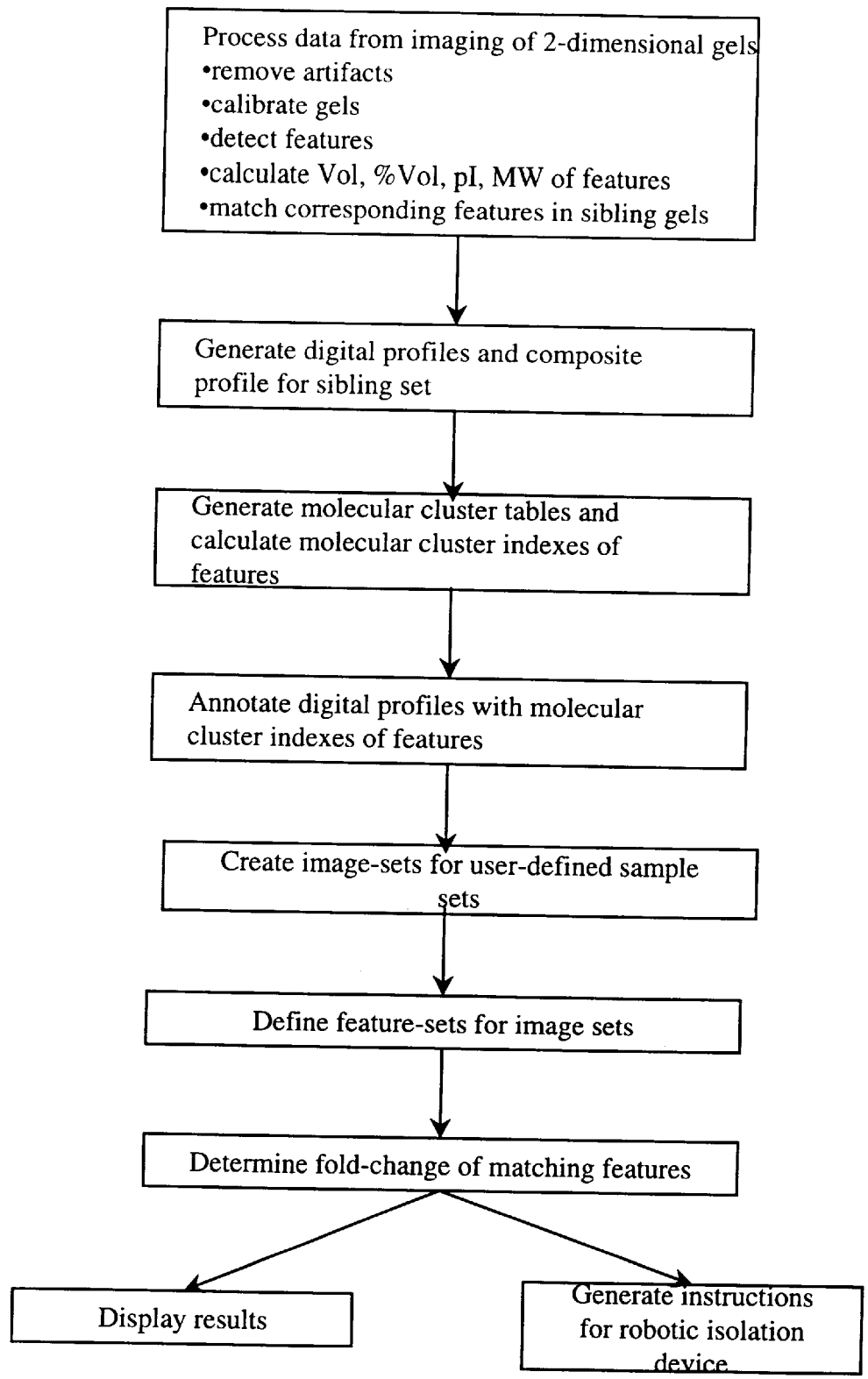
FIG. 2 is a flow diagram illustrating functions that are performed by means of a computer in a particular embodiment of the present invention.

This profile can be traced to the actual stored gels that were used to generate images from which the synthetic composite image was constructed, so that proteins identified by computer analysis of profiles can be retrieved. The profile can also be traced back to the original sample or patient. The reproducibility of the gel system coupled with the correction made possible through the use of standards and landmarks followed by a matching of correlate spots to a master gel allows for the comparison of many gels run with the same or different samples at the same or different times. Moreover, the data assembled during collection of the original biological sample, as described in section 5.1, can be reunited with the gel data, allowing for the analysis of computer selected cross sections of the samples based on such information as age or clinical outcome. FIG. 2 presents a flow diagram illustrating computer-mediated analysis according to one particular embodiment of the present invention.

5.5.2. Cross-matching Between Samples

Data generated from analysis of different samples are now subjected to computer analysis. In a preferred embodiment, each significant feature is assigned an index (the "Molecular Cluster Index", "MCI") that identifies the molecular content of the feature and has the same value in matching features in all gels. For each type of sample, a "molecular cluster table" is created that uniquely defines the coordinate system onto which each gel is successively mapped. This approach obviates the NxN problem of attempting to match each gel with all the others in a set.

To generate a molecular cluster table, a representative gel is arbitrarily chosen to be a master gel, preferably one regarded as optimal for its sample type. A new entry in the molecular cluster table is created for each feature (molecular cluster) in the synthetic composite of the sibling set of which this representative gel is a member. Additional molecular clusters can be added to the table when they are observed in other gels but are not represented in the master table. Such other gels are known as "secondary masters".

In one embodiment, the MCI is calculated from the pI and MW of the feature, by a hierarchical quad-tree decomposition of the pI/MW space. First, a 2D grid is calculated that encompasses the entire pI/MW space. By way of example, and not of limitation, pI may take any value between 0 and 14, and MW may take any value between 1,000 and 1,000,000. Since the row position of a protein (representing its displacement on a gel) is approximately proportional to the log of its molecular weight, the grid positions are calculated with respect to the natural logarithm of the molecular weight, i.e. ln(MW). The 2D pI/ln(MW) space can be divided by serial bisection horizontally and vertically into successively smaller quadrants, each quadrant containing fewer features than its parent, until a resolution is reached where the number of features in each cell of the 2D space is unlikely to be greater than 1.

In one particular embodiment, 9 successive subdivisions are made, so that the whole pI/ln(MW) space is divided into 512 divisions both vertically and horizontally (RES=512). The MCI of a feature in a master gel is now calculated from the pI and MW in the master coordinate system by the following formula:

$$MCI=((int)((ln(MW_{max})-ln(MW))/dM)*8192+(int)(pI/dI))*8192/RES$$

where $ln(MW_{max})=14$; $ln(MW_{min})=7$; $dM=(ln(MW_{max})-ln(MW_{min}))/RES=0.013672$;

and $pI_{max}=14$; $pI_{min}=0$; $dI=(pI_{max}-pI_{min})/RES=0.027344$

The representative gels of all other samples of a given type may now be matched (using MELANIE®) with master and secondary master gels for that sample type. The digital profiles are then annotated by adding, for each matched feature, the MCI of the feature in the master or secondary master profile.

5.5.3. Differential Analysis of Profiles

Once the profiles have been annotated with MCIs, computer analysis can be performed to select one or more features representing proteins or other biomolecules of interest. Preferably, analysis is performed by comparing the synthetic composite profiles that arise from replicate analysis of sibling gels from a single sample.

An image-set is created from a user-selectable list of samples in the database. Each member of the image set comprises the synthetic composite profile of the sibling set and the master molecular cluster table used to match the features.

A feature-set is then defined, representing the set of features that have been found across an image set. An arbitrary threshold level X is designated for the feature-set; a given feature is defined to be part of the set if it occurs in (i.e., has the same MCI in) at least X % of the members of the image set. For each member of the feature-set, the following attributes are defined: (1) the MCI, (2) the Mean % Vol (the average % Vol for all members of the image-set in which the feature occurs), (3) the Median % Vol, and (4) the number of images in the set in which the feature was identified.

Binary set operations may now be performed to compare sets of features between two image sets (referred to as the "background" and "foreground" sets). The basic binary operation is the calculation of fold-change between matching features in two feature-sets. Fold-change (G) is determined by the following algorithm: Let V1 and V2 be the Mean % Vol of a feature in background feature-set F1 and foreground feature-set F2 respectively, (where an absent feature is represented by V=0), then:

G=V2/V1 (where V2>V1)

G=V1/V2 (where V1>V2)

G=+MAX_G (where V1=0)

G=−MAX_G (where V2 =0), where MAX_G is some suitably large number.

This algorithm can optionally be performed using Median % Vol instead of Mean % Vol in the fold-change calculation. The result can be reported as a bar chart or in any other convenient format.

Serial set operations can be performed to determine the variation in expression of each feature in a feature-set as a function of some sample registration variable. For example, such comparisons can be used for (a) a time series study of expression variation in a set of sample donors; (b) a comparison of expression variation for sets of individuals with different diseases; or (c) a comparison of expression variation for sets of individuals on different therapies. A serial set operation generates a matrix of results where the rows enumerate the individual members of the feature-set, the columns enumerate different image-sets and the cells in the matrix contain numbers calculated from the Mean % Vol of each feature in each image set as described above.

For example, to compare a feature, designated MCI(F), over three image-sets, designated S1, S2 and S3, the % Vol of MCI(F) for each sample, V1, V2 and V3, are calculated as the Mean % Vol for MCI(F) in the corresponding image-set. Next, the mean, median and maximum V1, V2 and V3 are calculated across the row. Where a sample set does not contain MCI(F), the corresponding % Vol is taken as zero. The user selects a reference column, Vref, which may be any of the image-sets or the mean or the median. Then each cell is calculated as follows:

P1=(V1−Vref)/Vmax

P2=(V2−Vref)/Vmax

P3=(V3−Vref)/Vmax.

These values all lie in the range −1.0 to +1.0. This range may be divided into any desired number of subranges (e.g. seven equal subranges) and the result displayed graphically, with the values in the cells represented by a symbol for each subrange.

Computer-mediated comparison according to operator-specified criteria facilitates the rapid and efficient analysis of large numbers of profiles and permits the identification of small differences between profiles being compared even though each profile may represent many hundreds or thousands of detected biomolecules. The capacity for rapid and efficient manipulation of large sample sets enhances the likelihood of detecting statistically significant differences.

It should also be appreciated that the practitioners of the invention can add each newly generated profile to a continually growing database, allowing for cross-experiment comparisons, possibly in combinations unimagined by the original researchers. Profile databases may allow for virtual experiments to be run, wherein profiles from any study can be compared with profiles from any other study, without having to reproduce the actual clinical data. For example, any database which provides molecular weights and isoelectric points for proteins can be compared with a profile of the invention derived from analysis of proteins.

One skilled in the art can appreciate the many forms such an analysis can take, and the following examples are provided by way of illustration and not limitation.

The profiles of diseased and normal individuals can be compared to identify patterns of spots which consistently differ between the two populations. Said spots can contain proteins of therapeutic or diagnostic significance.

The profiles of diseased and normal tissue from a single individual can be compared to identify patterns of spots which consistently differ between the diseased and normal tissue. Said spots can contain biomolecules of interest for therapeutic or diagnostic purposes. This has the particular advantage of controlling for variation between different individuals as the comparison is made between samples taken from a single individual.

The profiles of treated and non-treated individuals can be compared to identify patterns of spots which correlate with a certain therapy or drug treatment. This may be helpful in elucidating drug mechanisms, in studying drug resistance or in drug development.

A three way comparison of healthy, diseased, and treated diseased individuals can identify which drugs are able to restore a diseased profile to a one that more closely resembles a normal profile. This can be used to screen drugs, to monitor the efficacy of treatment and to detect or predict the occurrence of side effects, whether in a clinical trial or in routine treatment, and to identify which spots are more important to the manifestation and treatment of a disease.

A three way comparison of diseased individuals who are untreated, treated with drug A, or treated with drug B can also identify interesting biomolecules. For example, if A is known to be effective and B is known to be ineffective, then biomolecules that differ between treatment group A (on the one hand) and both the untreated group and treated group B (on the other hand) are useful for prognosis and are candidates for study as therapeutic targets.

5.6. Removal of Selected Portions of a Supported Gel

It is a characteristic of the supported gel of invention that, once separated, the biomolecules are held in a stable array. A portion of the gel containing a single detected feature can now be removed without affecting the spatial integrity of the remainder of the array. By way of example, removal may be accomplished by excision of a portion of the gel, by localized application of an agent that liquefies the gel so that the desired species can be removed by suction or allowed to drip out, or by localized application of an electro-elution device. Removal of portions of the gel containing species that are required for analysis can be conducted accurately and reproducibly on the basis of the profile; such portions can be removed from a gel that has been imaged or from a duplicate or other replicate of an imaged gel. It will be readily appreciated that this is very suitable for computer-controlled analysis and selection.

Preferably, selected gel portions are excised using apparatus of the invention. Thus, a robotic device can be provided, under the control of software that uses as its reference the biological molecule profile obtained following separation of the biomolecules. This device can be operatively connected with a computer and driven by machine-readable instructions to perform excisions and manipulations on a gel in an operator-independent manner according to instructions generated by computer-mediated analysis of a plurality of profiles derived from analysis of a plurality of mixtures of biomolecules. The computer programs x,y movements and directs a cutting head of the robotic device to take a single cut or a series of overlapping cuts to isolate and remove an identified feature.

Figure 3:
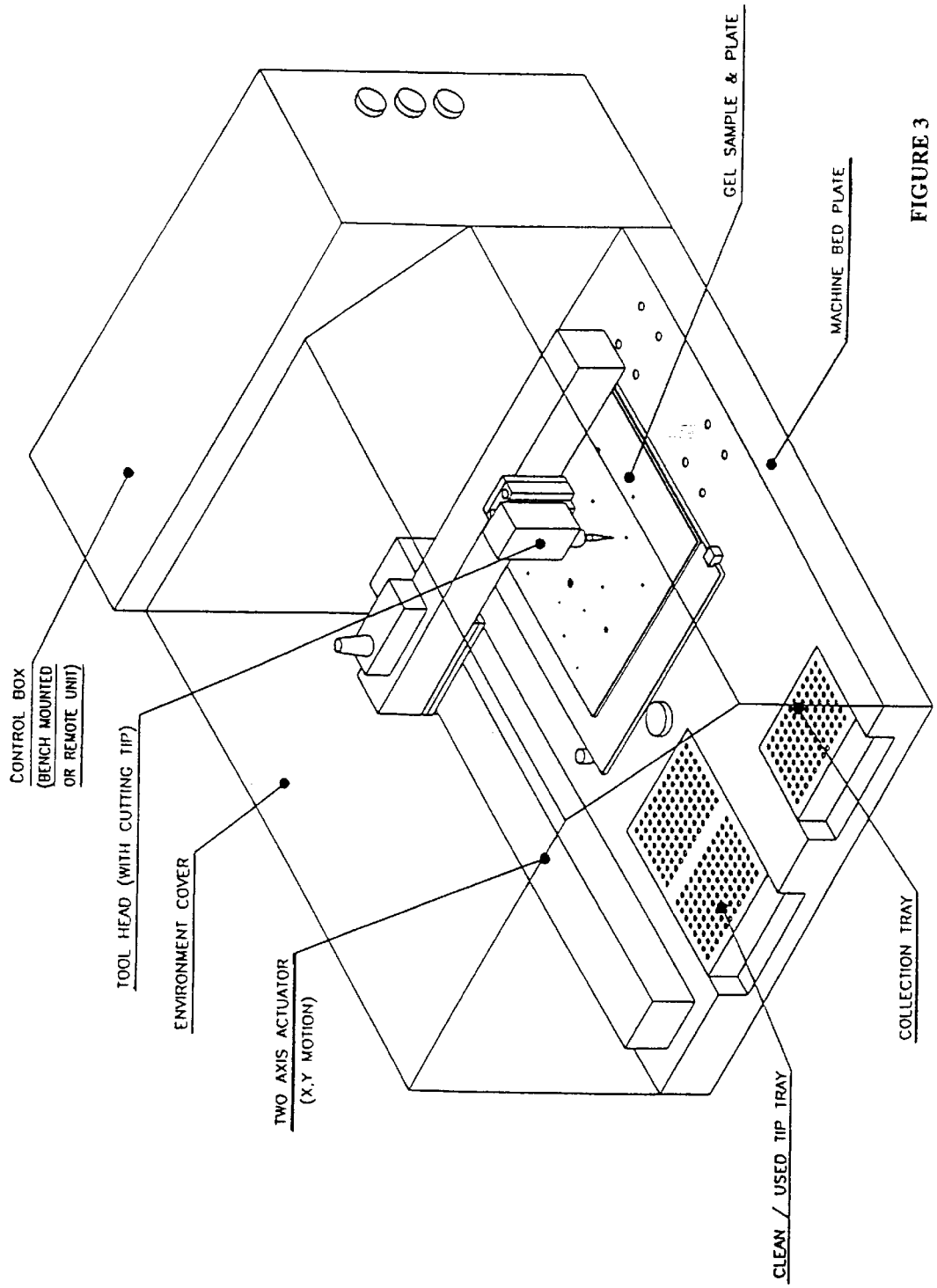
FIG. 3 is a diagram of a robotic device for isolating biomolecules from the supported gel of the present invention.

Such a device may comprise (1) a defined frame identical with or matched to the frame in which the gel was placed during imaging (2) a bed for controlled location of the frame with gel; and (3) a movable x,y coordinate-locating mechanism with drive attached to a changeable manipulating and excision component which is directed through software for locating gel regions of interest prescribed by an operator and is capable of performing the desired manipulation(s) and delivering gel or gel-derived material to a defined position in a receiving chamber. One embodiment of such a device is illustrated in FIG. 3.

This instrument is capable of removing gel fragments from a glass-backed gel and transferring the removed fragments into a suitable vessel. A separate reaction vessel (e.g. an Eppendorf vial) may be used for each gel fragment; more preferably, gel fragments are transferred to a rack of test tubes or to chambers in a multi-capacity vessel such as a 96-well collection microplate. The glass-backed gel to be manipulated is fitted onto guides on the bed of the instrument, thus aligning the glass, and hence the gel, with the cutting mechanism. The instrument removes one or more selected portions of the gel in accordance with machine-readable instructions. In one embodiment, a fresh tip is selected for each feature and a process of core-cutting, shearing and sucking is applied to break the gel's bond to the glass and remove the gel fragment. Preferably, the shearing process comprises tip movement from side to side along a first axis, followed by tip movement from side to side along a second axis at an angle (most preferably a right angle) to the first axis. Each gel fragment is transferred to the collection plate and then ejected, preferably into liquid to assist the removal of the gel fragment from the tip. Preferably, a mobile shuttle is contained within the tip for the dual purpose of preventing the gel fragment from being sucked into the vacuum pump during the cutting process and also to push the gel fragment out of the tip during ejection. To minimize carryover between different features, the cutting implements can be cleaned in an integral automated cleaning station. More preferably, the cutting implements are changed so that a new cutting implement is used for each feature, thereby preventing any carryover.

Large features are excised by making a plurality of adjacent or overlapping cuts, all pieces of the same feature being deposited in the same well of the collection plate, or different pieces of the feature being deposited in different wells. Alternatively, a profile is cut around the perimeter of the large feature; the gel is then lifted whilst applying a cutting action under the gel to separate it from the support, and the entire feature is transferred to the collection vessel. The system has been configured to allow multiple gels to be cut into one collection plate and also permits a gel to be cut into any number of collection plates, thus permitting all features to be further processed. Once the collection plate is full or complete, it is ready for further processing or can be stored. After selected gel fragments have been excised, the remainder of the gel can be stored, for instance at reduced temperature as described above.

5.7. Processing Removed Portions of the Gel

One or more removed portions of the gel are delivered to a workstation, for instance a general modular chemistry unit that is fully programmable and configured for proteolysis. This workstation permits the operation of any protocol that involves reagent addition, pipetting and transfer, incubation, mixing, chilling, vacuum drying and solid-phase extraction techniques, or any other technique for which a module can be developed. Plates are fitted onto carriers which are repositioned on the bed of the instrument by means of an integrated carrier manipulator. Such plates may take any form, preferably an orthogonal matrix of wells, and more preferably a 9 mm pitch microplate format. Especially preferred is a microplate with nozzles in the base of each well that allow liquid to pass through, such as those manufactured by Porvair Ltd., Shepperton, United Kingdom. In such a microplate, liquid and gel pieces are retained by a teflon frit and liquid is extracted through the frit by means of air pressure applied from above by the pipetting unit. This liquid may be sent to waste or, during peptide elution, collected in a second plate located under the nozzles during the extraction process.

A protein isolated according to the present invention can be analyzed, as described below, or can be administered to an experimental animal, such as a mouse, rat, or rabbit, for production of polyclonal or monoclonal antibodies against the isolated protein. Such antibodies are useful in diagnostic and prognostic tests and for purification of large quantities of the protein, for example by antibody affinity chromatography.

5.8. Analysis of Proteins

The workstation can be programmed for chemical proteolysis or enzymatic proteolysis using one or more suitable enzymes (e.g. trypsin or chymotrypsin) singly or in combination. See, e.g., Shevchenko et al., 1996, Analytical Chemistry 68: 850–858 and Houthaeve et al., 1995, FEBS Letters 376: 91–94 (each of which is incorporated herein by reference in its entirety). If desired, electro-elution can optionally be used to extract proteins from gel slices. In a preferred embodiment, the workstation is programmed so that each protein in a removed gel fragment is cleaved to generate a pool of peptides suitable for further characterization. Thus, the workstation receives samples of cut gel pieces in a suitable rack, and these pieces are subjected to steps of washing, reduction, alkylation, washing, and trypsinolysis. The resulting peptides are extracted into a second plate for further cleaning or additional preparation prior to analysis. See, e.g., Shevchenko, op. cit. Incubations may be performed at any temperature up to 100° C. and above; the workstation includes a sealing mechanism to prevent or minimize liquid loss when incubation is performed at a high temperature or for a prolonged period. The unit is designed to operate unattended, ideally overnight, and has comprehensive sensing, monitoring and self-checking mechanisms to ensure that the programmed protocol is performed correctly, to report any error, and to interrupt processing upon the occurrence of a previously specified contingency. Multiple plates can be processed in parallel and can if desired be processed according to different protocols. The workstation is also capable of peptide clean-up and other processes such as hydrazinolysis and labelling.

5.8.1. Determination of Amino Acid Sequences

The amino acid sequences of one or more peptides derived from a removed protein can now be determined, for instance by a suitable mass spectrometry technique, such as matrix-assisted laser desorption/ionization combined with time-of-flight mass analysis (MALDI-TOF MS) or electrospray ionization mass spectrometry (ESI MS). See Jensen et al., 1977, Protein Analysis By Mass Spectrometry, In Creighton (ed.), Protein Structure, A Practical Approach (Oxford University Press), Oxford, pp. 29–57; Patterson & Aebersold, 1995, Electrophoresis 16: 1791–1814; Figeys et al., 1996, Analyt. Chem. 68: 1822–1828 (each of which is incorporated herein by reference in its entirety). Preferably, a separation technique such as HPLC or capillary electrophoresis is directly or indirectly coupled to the mass spectrometer. See Ducret et al., 1996, Electrophoresis 17: 866–876; Gevaert et al., 1996, Electrophoresis 17: 918–924; Clauser et al., 1995, Proc. Natl. Acad. Sci. USA 92: 5072–5076 (each of which is incorporated herein by reference in its entirety). Especially preferred is the de novo sequencing technique described in U.S. patent application Ser. No. 08/877,605, which is incorporated herein by reference in its entirety. In de novo sequencing, the molecular mass of the peptide is accurately determined by any suitable technique, preferably with a mass spectrometer. A computer is used to determine all possible combinations of amino acids that can sum to the measured mass of the peptide, having regard to water lost in forming peptide bonds, protonation, other factors that alter the measured mass of amino acids, and experimental considerations that constrain the allowed combinations of amino acids. The computer then constructs an allowed library of all linear permutations of amino acids in the permitted combinations. Theoretical fragmentation spectra are then calculated for each member of the allowed library of permutations and are compared with an experimental fragmentation spectrum obtainable by mass spectrometry for the unknown peptide to determine the amino acid sequence of the unknown peptide. Most preferably, tandem mass spectrometry is used to determine the amino acid sequence of the unknown peptide.

Once the entire or a partial amino acid sequence of an isolated protein has been experimentally determined, a computer can be used to search available databases for a matching amino acid sequence or for a nucleotide sequence, including an expressed sequence tag (EST), whose predicted amino acid sequence matches the experimentally determined amino acid sequence. If no matching nucleotide sequence is found, a degenerate set of nucleotide sequences encoding the experimentally determined amino acid sequence can be reverse-engineered by techniques well known in the art; such a degenerate set of nucleotide sequences is useful for cloning the gene that encodes the isolated protein and for expressing the sequenced protein or peptide fragment. Alternatively, a subset of the degenerate set of nucleotide sequences can be reverse-engineered, using only codons that are preferred in the species from which the protein was obtained (e.g. codons preferred in humans, where the protein is a human protein); if desired, this subset can be restricted to the one nucleotide sequence that is most highly preferred in the relevant species.

Where a gene encoding an isolated protein is identified in a public or private database, the gene can be cloned and introduced into bacterial, yeast or mammalian host cells. Where such a gene is not identified in a database, the gene can be cloned, using a degenerate set of probes that encode an amino acid sequence of the protein as determined by the methods and apparatus of the present invention. Where a database contains one or more partial nucleotide sequences that encode an experimentally determined amino acid sequence of the protein, such partial nucleotide sequences (or their complement) serve as probes for cloning the gene, obviating the need to use degenerate sets.

Cells genetically engineered to express such a recombinant protein can be used in a screening program to identify other proteins or drugs that specifically interact with the recombinant protein, or to produce large quantities of the recombinant protein, e.g. for therapeutic administration. Possession of the cloned gene permits gene therapy to replace or supplement a protein whose absence or diminished expression is associated with disease. Possession of the cloned gene likewise permits antisense or triple-helix therapy to suppress expression of a protein whose presence or enhanced expression is associated with disease.

5.8.2. Analysis of Post-translational Processing

Many proteins undergo post-translational modification with chemical groups other than amino acids, e.g. phosphate groups and oligosaccharides. The presence, location, and chemical identity of such groups on a protein can be analyzed using the protein-specific peptide fragments obtained by the apparatus and methods of the present invention. In one embodiment, a peptide pool obtained from an isolated protein in a gel fragment is divided. One portion is used for identification of the protein as described in section 5.8.1 above. The other portion or portions are used to identify individual post translational modifications by standard methods known to the art. For example, phosphorylation analysis is described in Carr et al., 1996, Analyt. Biochem. 239: 180–192 and Townsend et al., 1996, Protein Science 5: 1865–1873 (each of which is incorporated herein by reference in its entirety). Glycan analysis is described in Dwek et al., 1993, Analyt. Biochem. 62: 65–100 (incorporated herein by reference in its entirety) and in the references cited in section 5.3 above.

6. EXAMPLE: PROTEINS FROM SERUM AND SYNOVIAL FLUID OF PATIENTS WITH RHEUMATOID ARTHRITIS

Proteins in serum and synovial fluid from patients with rheumatoid arthritis (RA) were separated by isoelectric focusing followed by SDS-PAGE and compared.

6.1. Isoelectric Focusing

For isoelectric focusing (IEF), each sample was applied to an Immobiline® DryStrip Kit (Pharmacia BioTech), following the procedur e described in the manufacturer's instructions, see Instructions for Immobiline® DryStrip Kit, Pharmacia, #18-1038-63, Edition AB (incorporated herein by reference in its entirety), with optional modifications as described by Sanchez et al. 1997, Electrophoresis 18: 324–327 (incorporated herein by reference in its entirety). In certain cases, in order to increase the resolution in a particular pH range or to load a larger quantity of a target protein onto the gel, a narrow-range "zoom gel" having a pH range of 2 pH units or less was used, according to the method described in Westermeier, 1993, Electrophoresis in Practice (VCH, Weinheim, Germany), pp. 197–209 (which is incorporated herein by reference in its entirety).

6.2. Gel Equilibration and SDS-PAGE

IEF gels were prepared for SDS-PAGE by equilibration in a SDS buffer system according to a two step procedure comprising initial reduction of the disulfide bonds, followed by alkylation of the free thiol groups, as described by Sanchez et al., id. Thereafter, SDS-PAGE was carried out according to Hochstrasser et al., 1988, Analy tical Biochemistry 173: 412–423 (incorporated herein by reference in its entirety), with modifications as specified below.

6.3. Preparation of Supported Gels

Covalent attachment of SDS-PAGE gels to a glass support was achieved by applying a 0.4% solution of γ-methacryl-oxypropyltrimethoxysilane in ethanol to the glass plate ("the bottom plate") to which the gel was to be attached. Excess reagent was removed by washing with water, and the bottom plate was allowed to dry. At this stage, both as identification for the gel, and as a marker to identify the coated face of the plate, an adhesive bar-code was attached to the bottom plate in a position such that it would not come into contact with the gel matrix.

An opposing glass plate ("the top plate") was treated with RepelSilane (Pharmacia Biotech) to minimize gel attachment. After applying the reagent, the top plate was heated by applying a flow of heated air (e.g. from a hot air gun) to the surface of the plate. Excess reagent was again removed by water washing, and the top plate was allowed to dry.

The dried plates were assembled into a casting box with a capacity of 13 gel sandwiches. Several casting boxes can be assembled in parallel to cast more gels under the same conditions. The top and bottom plates of each sandwich were spaced by means of 1 mm thick spacers. The sandwiches were interleaved with acetate sheets to facilitate separation of the sandwiches after gel polymerization. Casting was then carried out according to Hochstrasser et al., op. cit.

6.4. SDS-PAGE

The gel strips from the IEF step were applied to the top of the poured SDS-PAGE gel and electrophoresis begun. In order to ensure even cooling of the gel during the electrophoresis run, a system was designed essentially as described by Amess et al,. 1995, Electrophoresis 16: 1255–1267 (incorporated herein by reference in its entirety). Even, efficient cooling is desirable in order to minimize thermal fluctuations during electrophoresis and hence to maintain the consistency of migration of the proteins. Electrophoresis was carried out until the tracking dye reached the bottom edge of the gel. The gels were then removed immediately for staining.

6.5. Staining

The top plate of the gel cassette was carefully removed, leaving the gel bonded to the bottom plate. The bottom plate with its attached gel was then placed into a staining apparatus, which has the capacity to accommodate 12 gels. The gels were completely immersed overnight in fixative solution, comprising 40% (v/v) ethanol, 10% (v/v) acetic acid, 50% (v/v) water. The fixative was then drained from the tank, and the gels were primed by immersion in 7.5% (v/v) acetic acid, 0.05% (w/v) SDS for 30 mins. The priming solution was then drained, and the gels were stained by complete immersion in the dye solution for 4 hours. A stock solution of fluorescent dye was prepared by diluting Sypro Red (Molecular Bioprobes, Inc., Eugene, Oreg.) according to the manufacturer's instructions. The diluted solution was filtered under vacuum though a 0.4 um filter.

In order to achieve a continuous, even circulation of the various solutions over all 12 gels, solutions were introduced into the tank via a distribution bar, extending along the bottom of the tank across its entire width and provided with holes that allow the solution to flow evenly over each of the gels.

6.6. Imaging of the Gel

A computer-readable output was produced by imaging the fluorescently stained gels with a Storm scanner (Molecular Dynamics, Sunnyvale, Calif.) according to the manufacturer's instructions, (see Storm User's Guide, 1995, Version 4.0, Part No. 149–355, incorporated herein by reference in its entirety) with modifications as described below. Since the gel was rigidly bonded to a glass plate, the gel was held in contact with the scanner bed during imaging. To avoid interference patterns arising from non-uniform contact between the gel and the scanner bed, a film of water was introduced under the gel, taking care to avoid air pockets. Moreover, the gel was placed in a frame provided with two fluorescent buttons that were imaged together with the gel to provide reference points (designated M1 and M2) for determining the x,y coordinates of other features detected in the gel. A matched frame was provided on a robotic gel excisor in order to preserve accurate alignment of the gel. After imaging, the gels were sealed in polyethylene bags containing a small volume of staining solution, and then stored at 4° C.

The output from the scanner was first processed using MELANIE® to autodetect the registration points, M1 and M2; to autocrop the images (i.e., to eliminate signals originating from areas of the scanned image lying outside the boundaries of the gel, e.g. the reference frame); to filter out artifacts due to dust; to detect and quantify features; and to create image files in GIF format. Features were detected by a computer-mediated comparison of potential protein spots with the background to select areas of the gel associated with a signal that exceeded a given threshold representing background staining.

A second program was used for interactive editing of the features detected and to match duplicate gels for each sample. First, images were evaluated to reject images which had gross abnormalities, or were of too low a loading or overall image intensity, or were of too poor a resolution, or where duplicates were too dissimilar. If one image of a duplicate was rejected then the other image belonging to the duplicate was also rejected regardless of image quality. Samples that were rejected were scheduled for repeat analysis.

Landmark identification was used to correct for any variability in the running of the gel. This process involves the identification of certain proteins which are expected to be found in any given biological sample. As these common proteins exhibit identical isoelectric points and molecular weight from sample to sample, they can be used as standards to correct for any possible gel variation or distortion. The pI and molecular weight values for the landmarks in the reference gel were determined by co-running a sample with E. coli proteins which had previously been calibrated with respect to known protein in human plasma. Features which were considered to be artifacts, mainly at the edges of the gel image and particularly those due to the sample application point and the dye-front, were removed. Duplicate gels were then aligned via the landmarks and a matching process performed so as to pair identical spots on the duplicate gels. This provided increased assurance that subsequently measured isoelectric points and molecular weights were accurate, as paired spots demonstrated the reproducibility of the separation. The corrected gel, in addition to being used for subsequent analysis, was printed out for visual inspection.

Generation of the image was followed by computer measurement of the x,y coordinates of each protein, which were correlated with particular isoelectric points and molecular weights by reference to the known landmark proteins or standards. A measurement of the intensity of each protein spot was taken and stored. Each protein spot was assigned an identification code and matched to a spot on a master gel, i.e., a reference gel which contained most or all of the protein spots seen in each type of sample and was used as a template to which the protein spots of the other samples were matched. This step allowed for the identification of putative correlate spots across many different gels. The data collected during collection of the original biological sample, as described in section 5.1, were reunited with the gel data, thereby permitting the analysis of computer selected cross-sections of the samples based on information such as age or clinical outcome.

The end result of this aspect of the analysis was the generation of a digital profile which contained, for each identified spot: 1) a unique arbitrary identification code, 2) the x,y coordinates, 3) the isoelectric point, 4) the molecular weight, 5) the signal value, 6) the standard deviation for each of the preceding measurements, and 7) a pointer to the MCI of the spot on the master gel to which this spot was matched. By virtue of the LIMS, this profile was traceable to the actual stored gel from which it was generated, so that proteins identified by computer analysis of gel profile databases could be retrieved. The LIMS also permitted the profile to be traced back to the original sample or patient.

6.7. Digital Analysis of the Gel

Once the profile was generated, analysis was directed toward the selection of interesting proteins.

The protein features in the individual images from the paired serum and synovial fluid samples were compared electronically. Molecular identity of any one feature across the set of images is defined in this analysis as identity of position in the 2-D separation. Quantitative measurement of the abundance of an individual feature in an individual image was based on normalized fluorescence intensity measured for that feature in that image. Those proteins whose abundance differed between the sets of serum and synovial fluid samples were revealed by electronic comparison of all detected features in all relevant images.

6.8. Recovery and Analysis of Selected Proteins

Differentially expressed proteins were robotically excised and processed to generate tryptic peptides; partial amino acid sequences of these peptides were determined by mass spectroscopy, using de novo sequencing.

6.9. Results

These initial experiments identified 12 proteins that were present at higher levels in human RA synovial fluid than in matched serum samples, and 9 proteins that were present at lower levels in human RA synovial fluid than in matched serum samples. Partial amino acid sequences were determined for each of these differentially expressed proteins. Computer analysis of public databases revealed that 16 of these partially sequenced proteins were known in the art and that 5 were not described in any public database examined.

7. CONCLUSION

As will be apparent to those skilled in the art, the following are amongst the objects of the present invention:

1. A supported gel suitable for use in electrophoresis, in which the gel is covalently bonded to a solid support such that the gel has two-dimensional spatial stability, and the support is substantially non-interfering with respect to detection of a detectable label carried by the species.

2. A supported gel according to claim 1, wherein the support is glass.

3. A supported gel according to claim 1 or claim 2, herein the gel is polyacrylamide.

4. A supported gel according to any preceding claim, herein the gel and the support are bonded via a bifunctional linker.

5. A supported gel according to claim 4, obtainable by functionalising the support, and casting the gel onto the functionalised support.

6. A supported gel according to any preceding claim, herein the label is fluorescent.

7. A supported gel according to any preceding claim, including a plurality of separated labelled species.

8. A supported gel according to claim 7, wherein the species are proteinaceous.

9. A supported gel according to claim 7 or claim 8, from which one or more portions have been removed, without affecting the spatial stability of the gel.

10. An assay for labelled species by gel electrophoresis, which comprises separating the species on a gel according to any of claims 1 to 6, removing one or more potions of the gel containing separated species, without affecting the spatial stability of the gel, and analyzing the species in said one or more portions.

11. Apparatus for use in analyzing species separated on a gel, which comprises:

means for detecting the array of species on the gel, the gel being fixed to a support that is substantially non-interfering with respect to the detection of a detectable label carried by the species;

selecting one or more points of the array, as containing species for analysis;

removing the gel at each of said one or more points; and analyzing the contents of the removed gel.

12. Apparatus according to claim 11, which comprises robotic means for excising discrete portions of the gel.

13. Apparatus according to claim 11 or claim 12, wherein the gel is a supported gel according to any of claims 1 to 8.

14. An automated, integrated process for analysis of species in a biological sample, which comprises:

(a) separating the species by applying the contents of the sample to a gel, the gel being fixed to a support that is substantially non-interfering with respect to the detection of a detectable label carried by the species;

(b) mapping the resultant array of species;

(c) selecting a point of the array, as containing species for analysis;

(d) removing gel at the selected point;

(e) analyzing the contents of the removed gel; and (f) repeating steps (c), (d) and (e), for another point of the array, thereby recovering and characterizing individual species.

15. A supported gel according to claim 4, in which the bifunctional linker does not comprise at least one positively charged amino compound.

16. A supported gel according to claim 15, in which the bifunctional linker does not comprise a charged amino polymer.

The present invention is not to be limited in terms of the particular embodiments described in this application, which are intended as single illustrations of individual aspects of the invention. Functionally equivalent methods and apparatus within the scope of the invention, in addition to those enumerated herein, will be apparent to those skilled in the art from the foregoing description and accompanying drawings. Such modifications and variations are intended to fall within the scope of the appended claims.

We claim:

1. A computer-assisted method for selecting and directing the isolation of one or more biomolecules present in a two-dimensional array, comprising:

imaging said two-dimensional array or a replica thereof to generate a computer-readable output comprising, for each of a plurality of biomolecules detected in said two-dimensional array, a pair of x,y coordinates and a signal value;

processing said output in at least one computer to select one or more of said detected biomolecules in accordance with previously ordained or operator-specified criteria; and generating machine-readable instructions that direct a robotic device to isolate at least one of said selected biomolecules from said two-dimensional array.

2. The method according to claim 1, further comprising:

isolating at least one of said selected biomolecules from said two-dimensional array by means of said robotic device in accordance with said machine-readable instructions.

3. The method according to claim 2, further comprising, prior to said imaging:

a first separation step, wherein a plurality of biomolecules present in a biological sample are separated according to a first physical or chemical property to form a one-dimensional array of biomolecules;

a second separation step, wherein said one-dimensional array of biomolecules is separated according to a second physical or chemical property to form said two-dimensional array.

4. The method according to claim 3, wherein said first separation step results in a discontinuous one-dimensional array.

5. The method according to claim 1, wherein said machine-readable instructions direct x and y movements of said robotic device.

6. The method according to claim 5, further comprising: isolating at least one of said selected biomolecules from said two-dimensional array by means of said robotic device in accordance with said machine-readable instructions.

7. The method according to claim 6, further comprising, prior to said imaging:

a first separation step, wherein a plurality of biomolecules present in a biological sample are separated according to a first physical or chemical property to form a one-dimensional array of biomolecules;

a second separation step, wherein said one-dimensional array of biomolecules is separated according to a second physical or chemical property to form said two-dimensional array.

8. The method according to claim 5, wherein said processing is in accordance with previously ordained criteria.

9. The method according to claim 5, wherein said processing is in accordance with operator-specified criteria.

10. The method according to claim 5 or 6, in which said biomolecules are oligosaccharides.

11. The method according to claim 5 or 6, in which said biomolectles are proteins.

12. The method according to claim 11, in which said proteins are glycoproteins.

13. The method according to claim 11, in which said two-dimensional array is contained in a polyacrylamide gel.

14. The method according to claim 13, in which said proteins have been separated by isoelectric focusing, followed by electrophoresis in the presence of sodium dodecyl sulfate.

15. The method according to claim 13, in which said polyacrylamide gel is bonded to a generally planar solid support such that the gel has two-dimensional spatial stability, and the support is substantially non-interfering with respect to detection of a detectable label carried by the proteins.

16. The method according to claim 15, in which said polyacrylamide gel is covalently bonded to said solid support.

17. The method according to claim 16, in which said detectable label is a fluorescent label.

18. The method according to claim 17, in which said solid support is glass.

19. Apparatus for computer-assisted isolation of one or more selected biomolecules present in a two-dimensional array, comprising:

a detector capable of imaging said two-dimensional array to generate a computer-readable output comprising, for each of a plurality of biomolecules in said two-dimensional array, a pair of x,y coordinates and a signal value;

one or more computers programmed to select one or more biomolecules represented in said output in accordance with previously ordained or operator-specified criteria and to generate machine-readable instructions that direct a robotic device to isolate at least one of said selected biomolecules; and a robotic device capable of isolating at least one of said selected biomolecules in accordance with said instructions, wherein said detector is operably connected to at least one of said one or more computers, and at least one of said one or more computers is operably connected to said robotic device.

20. The apparatus according to claim 19, wherein said machine-readable instructions direct said robotic device to perform x and y movements and said robotic device is capable of performing x and y movements in accordance with said instructions.

21. The apparatus according to claim 20, in which said separated biomolecules are proteins.

22. The apparatus according to claim 21, in which said two-dimensional array is contained in a polyacrylamide gel.

23. The apparatus according to claim 22, in which said polyacrylamide gel is bonded to a generally planar solid support such that the gel has two-dimensional spatial stability, and the support is substantially non-interfering with respect to detection of a detectable label carried by the proteins.

24. The apparatus according to claim 23, in which said polyacrylamide gel is covalently bonded to said solid support.

25. The apparatus according to claim 23, in which said detectable label is a fluorescent label.

26. The apparatus according to claim 25, in which said solid support is glass.

* * * * *